United States Patent [19]

Goisser et al.

[11] Patent Number: 5,388,988
[45] Date of Patent: Feb. 14, 1995

[54] DENTAL INSTRUMENT FOR TREATING TEETH WITH A LASER BEAM

[75] Inventors: Siegfried Goisser, Einhausen; Lutz Beerstecher, Bensheim; Ralf Sutter, Weinheim, all of Germany

[73] Assignee: Siemens Aktiengesellschaft, Munich, Germany

[21] Appl. No.: 100,134

[22] Filed: Aug. 2, 1993

[30] Foreign Application Priority Data

Aug. 10, 1992 [DE] Germany ............................. 4226461

[51] Int. Cl.$^6$ ........................... A61C 1/00; A61C 3/00
[52] U.S. Cl. ........................................ 433/29; 606/17; 606/22
[58] Field of Search ....................... 433/29, 215; 606/2, 606/3, 10, 13, 14, 15, 16, 17, 18, 19, 22, 23

[56] References Cited

U.S. PATENT DOCUMENTS

| | | | |
|---|---|---|---|
| 3,906,953 | 9/1975 | Wallace et al. | 606/18 X |
| 4,211,229 | 7/1980 | Wurster | 606/18 X |
| 4,503,853 | 3/1985 | Ota et al. | |
| 4,733,660 | 3/1988 | Itzkan | 606/17 X |
| 4,826,431 | 5/1989 | Fujimura et al. | |
| 4,836,782 | 6/1989 | Gonser | 433/215 X |
| 4,849,859 | 7/1989 | Nagasawa | 606/18 X |
| 5,118,293 | 6/1992 | Levy | |
| 5,300,067 | 4/1994 | Nakajima et al. | 606/17 X |

FOREIGN PATENT DOCUMENTS

| | | |
|---|---|---|
| 0073617 | 3/1983 | European Pat. Off. . |
| 0375578 | 6/1990 | European Pat. Off. . |
| 0523574 | 1/1993 | European Pat. Off. . |
| 0530574 | 3/1993 | European Pat. Off. . |
| 3637568 | 5/1988 | Germany . |
| 3800555 | 7/1989 | Germany . |
| 4038809 | 4/1992 | Germany . |
| 9204412 | 7/1992 | Germany . |

*Primary Examiner*—Gene Mancene
*Assistant Examiner*—Nicholas D. Lucchesi
*Attorney, Agent, or Firm*—Hill, Steadman & Simpson

[57] ABSTRACT

A dental instrument for treating teeth with a laser beam has an output by a transmission element arranged in the head part of the instrument. The instrument is supplied with a gaseous agent which is conducted at least at the application side across the optics, particularly across the optical boundary surface of the transmission element facing toward the light exit side and will then flow out of the head part into the beam exit direction.

12 Claims, 2 Drawing Sheets

DENTAL INSTRUMENT FOR TREATING TEETH WITH A LASER BEAM

BACKGROUND OF THE INVENTION

The present invention is directed to a dental instrument for treating teeth with laser beams that are directed from a transmission element arranged in a head part of a dental handpiece.

Dental instruments which utilize laser beams are disclosed by EP-A-375,578 and by German 3,800,555.

A problem with instruments that have an optical light exit window is that deposits, whether in the form of spray water, fog or ablation products from the preparation location, can form on the last optical boundary surface of the beam optics during the treatment. These deposits will deteriorate the light transmission capabilities of the optics. Thus, the efficiency as a consequence of the dampening effects of the deposits will be decreased and, in some instances, the deposits are even capable of damaging the optics.

In an arrangement disclosed by German Gebrauchsmuster 92,04,412, an attempt to overcome this problem has spray nozzles located in the proximity of the beam discharge for spraying cooling or cleaning liquid into the region immediately adjacent to the beam discharge in order, thus, to effect a cleaning of the discharge, on the one hand, and to effect a cooling of the material charged by the laser emission, on the other hand. The cleaning of the optical boundary surfaces of a beam optics with water is risky for two reasons. First, the water itself is always a carrier of contaminants and always contains superfine dirt or other particles that can precipitate at the boundary surface of the beam optics. A second problem is an undesirable dampening effect that will deteriorate the efficiency of the light transmission capabilities occurs when water strikes optical boundary surfaces from which a laser beam emerges.

SUMMARY OF THE INVENTION

The object of the present invention is to eliminate the problem with deposits on the optics.

To accomplish this object, the present invention is directed to a dental instrument for treating teeth with a laser beam that has an output from a transmission element arranged in a head part of the instrument, said instrument having means for supplying a gaseous agent which is conducted across the optics at least at the application side and essentially flows off from the head part in the beam exit direction.

A gaseous agent, preferably compressed air, is conducted practically across the last optical boundary surface of the optics from which the laser beam emerges, either directly as a free beam or indirectly via a waveguide. Thus, this boundary surface is rinsed by the agent and this rinsing agent or gas jet is subsequently conducted in the direction toward the preparation location so that deposits at the optics can be effectively prevented, even if a spray nozzle for water for cooling the preparation location were to be arranged in the region of the light exit.

When the laser beam emerges in a free beam, it is advantageous to provide a spacer of material that is not transparent for the laser emission employed. In this case, the transmission element will be a lens and the spacer immediately follows the lens. The spacer serves the purpose, first, of enabling an erosion in the optimum focal region and, second, serves as a protection against unintentional erosion of or, respectively, damage to the optical parts lying in the beam region. It is advantageous to provide a conical spacer for guiding the rinsing jet so that a precipitation of the ablation products or spray water fog on the relatively high-grade optics can, thus, be avoided at the beam exit. Another advantage is that the potentially scattered beams are effectively blanked out or blocked by the non-permeable material of the spacer.

When the laser beams are conducted into a waveguide following the transmission element, it is advantageous to provide a cover plate of material traversable by the laser beam between the last transmission element and the waveguide. The cover plate is advantageously introduced in an easily interchangeable fashion in the head housing with a seal element so that the gaseous agent can essentially flow off only over the waveguide. This flow will prevent precipitation from forming on the last boundary surface of the optics.

Other advantages and features of the invention will be readily apparent from the following description of the preferred embodiments, the drawings and claims.

DESCRIPTION OF THE PREFERRED EMBODIMENTS

Figure 1:
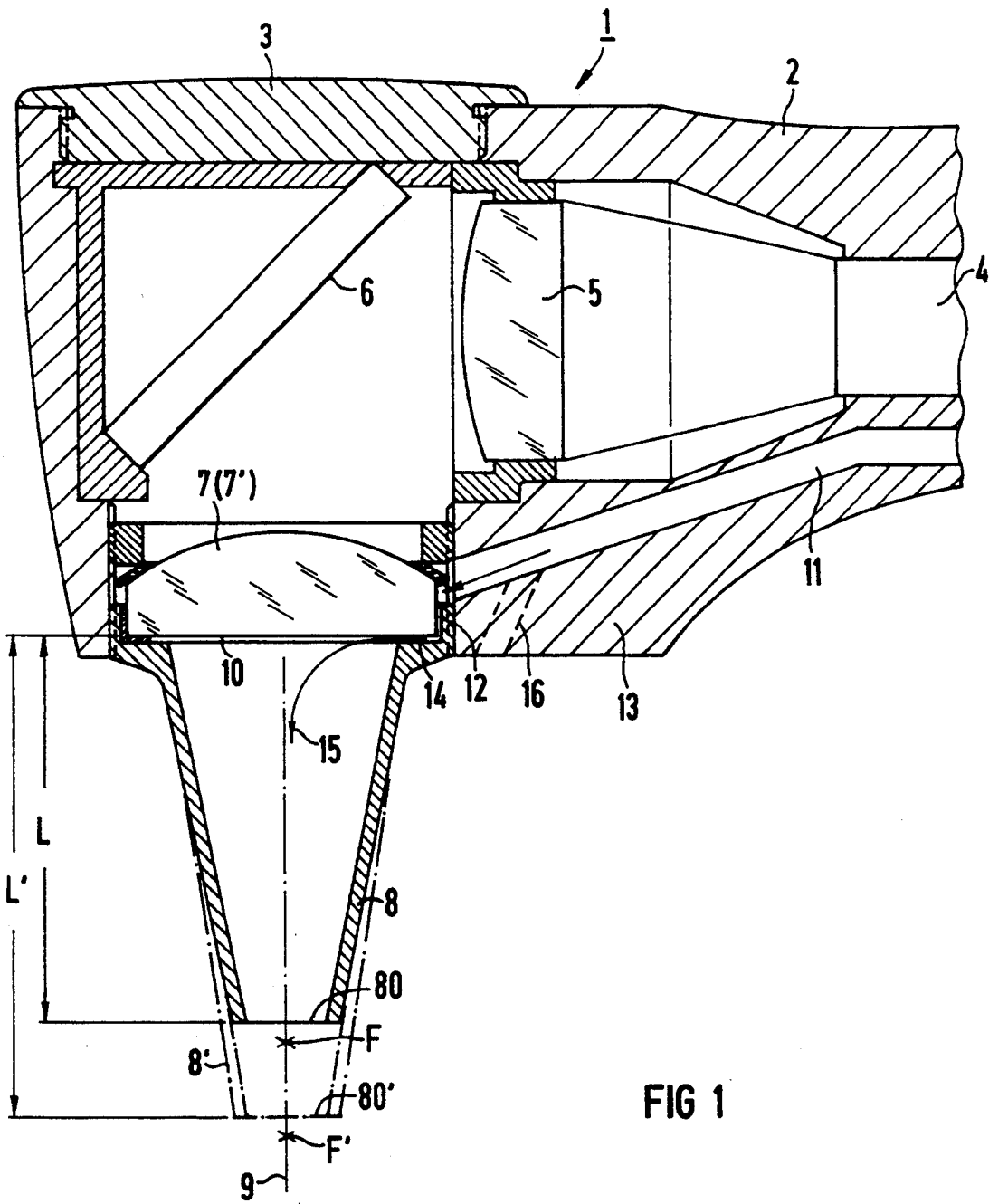
FIG. 1 is a cross sectional view of an end of a dental handpiece utilizing the improvements of the present invention with portions in elevation for purposes of illustration.

The principles of the present invention are particularly useful when incorporated in a dental instrument, generally indicated at 1. The dental instrument 1 includes an elongated gripping sleeve 2 in a known way that ends in a head part 3. A light conductor 4 is centrally arranged in the gripping sleeve 2 and this light conductor 4 is supplied by a laser beam source (not shown) which is arranged outside of the instrument. The laser beams emerging from the end face of the light conductor 4 will be directed, first, on a lens 5 which will direct these onto a deflecting mirror 6, wherein they are totally reflected. The laser beam is directed by the mirror 6 onto a second lens 7 that focuses the emerging beams onto a focal point F that is located immediately outside of a free end of a conical spacer 8 that is mounted on the head part 3.

In FIG. 1, two versions of the spacer that have different lengths and aperture widths are shown in the illustration with reference to the longitudinally symmetry on an axis 9 of the head housing 3. The spacer 8 which has a length L of approximately 10 mm and has an exit aperture 80 having a diameter of approximately 1 mm through 3 mm. The spacer 8' shown in dot-dash lines has a length L' which is approximately one-third larger than the length L. In this second version, the focal point F' will lie barely outside a cone aperture 80' and, thus, requires a lens 7' with a longer focal length.

The conical spacers 8 or 8' enable an optimum erosion of dental substance practically in the focal region. The spacer 8 or 8' is advantageously fabricated of a material that is non-transparent for the laser emission employed, for example it is made of metal. As a result, a good protection against unintentional erosion of subjects lying in the beam region as well as a blanking or blocking of potential scattered beams is established. Another critical useful effect lies in the optimum guidance of a gaseous agent which is conducted over the optical boundary surface 10 of the lens 7 in order to prevent deposits thereon. As indicated by arrows, the gaseous agent is first conducted into an interspace 12 between the lens 7 and the housing walls 13 of the head part 3 by a delivery channel 11 that is laid in a known way within the gripping sleeve 2. From this interspace 12, the gaseous agent will laterally rinse the lens 7 and is then subsequently steered transversely relative to the longitudinal axis 9 by an annular gap 14 that is formed between the lens 7 and a spacer 8. As a result of this, the optical boundary surface 10 of the lens 7 will be rinsed. The annular gap 14 has walls which form guide and baffle surfaces for the gaseous agent or rinse air and the gap 14 expediently contains baffle webs that are arranged so that part of the rinse air is conducted across the optical middle of the lens 7 so that the optical center, in particular, is optimally rinsed and is kept free of incident particles. Advantageously, the arrangement is undertaken so that an asymmetrical inflow of the rinse air will be established.

The conicity of the spacer 8 provides that the agent stream is optimally conducted in the direction of the exit aperture 80. The rinse agent here is advantageously compressed air that can be employed at the same time for forming a water/air mixture or spray that can emerge in a known way via the exit channel 16 that is directed onto the preparation location and is shown with broken lines in FIG. 1.

Figure 2:
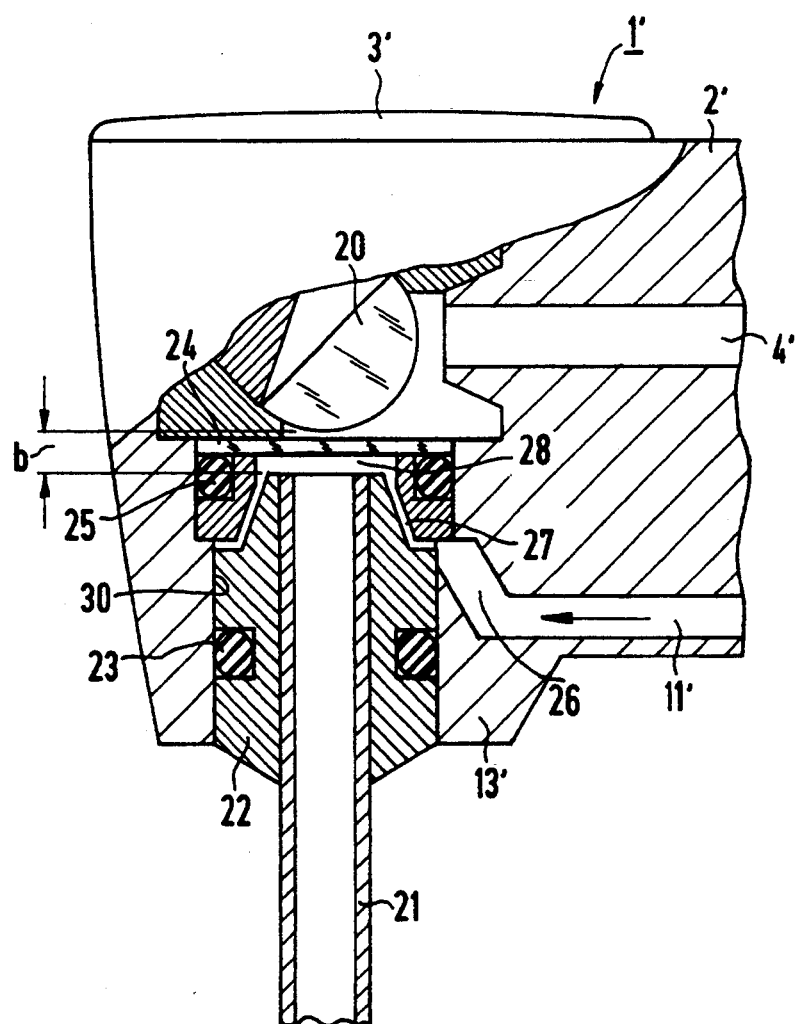
FIG. 2 is a cross sectional view with portions in elevation of a modification of the invention.

An alternative embodiment of the handpiece is generally indicated at 1' in FIG. 2 and has a transmission element 20 which unites the function both of the two lenses 5 and 7, as well as the deflecting mirror 6 of the previous embodiment of FIG. 1. The lens or element 20 is provided in the head part 3' of the instrument to receive the laser beam connected by a conductor 4' of a sleeve 2'. Whereas the light beam in the embodiment of FIG. 1 emerges from the lens 7 in a free beam, the beam emerging from the transmission element 20 is coupled into a hollow waveguide 21. The waveguide is secured to a mount 22 that is held in easily detachable and, thus, interchangeable fashion in a bore 30 of the head part 3' with an O-ring 23.

A cover plate 24 of a material that is transmissive for the laser emission employed is arranged at a spacing b required for the infeed of the beams between the light exit of the optical transmission element 20 and an entrance face of the waveguide 21. This cover plate 24 serves as an effective protection against deposits of ablation products or spray fogs on the boundary layer surface during the preparation or, respectively, against damage to the optics by these particles. The cover plate 24 is held in an easily replaceable fashion in the head part 3' with an O-ring 25. A further useful effect of the cover plate is that this forms a guide and baffle surface or channel with chambers 26, 27 and 28 together with the housing walls 13' of the head part and of the mount 22 by which the gaseous agent, particularly compressed air emerging from the delivery conduit 11', is guided into the waveguide 21. As a consequence of the air flow, it is seen to that the above-mentioned particles cannot proceed at all into the waveguide.

In conclusion, let it be pointed out that the light exit need not necessarily proceed in the direction of the longitudinal symmetry axis of the head housing but that, on the contrary, a lateral light exit at the free end of the waveguide 21 or, respectively, of the spacer 8 or 8' is conceivable. Accordingly, this is accomplished by providing suitable deflecting optics which are possible within the scope of the present invention.

Although various minor modifications may be suggested by those versed in the art, it should be understood that we wish to embody within the scope of the patent granted hereon all such modifications as reasonably and properly come within the scope of our contribution to the art.

We claim:

1. A dental instrument for treating teeth with laser beams, said dental instrument comprising a head part; a transmission element having a boundary surface being arranged in the head part for outputting the laser beams in a beam exit direction; and means for conducting a gaseous agent across said boundary surface and from the head part in the beam exit direction, said means directing the gaseous agent from adjacent a side of the boundary surface includes guide and baffle surfaces for directing the agent transversely across the boundary surface and finally into the beam exit direction.

2. A dental instrument according to claim 1, wherein the guide and baffle surfaces are arranged so that the gaseous agent flows asymmetrically into the region of said boundary surface.

3. A dental instrument for treating teeth with laser beams, said dental instrument comprising a head part; a transmission element being arranged in the head part for outputting the laser beams in a beam exit direction; a waveguide being provided immediately following the transmission element, said laser beam emerging from the transmission element being coupled into the waveguide; a cover plate of material that is transmissive for the light rays of the laser beam being provided at a spacing between the end of the waveguide and the transmission element, said cover plate having a boundary surface, and means for conducting a gaseous agent across the boundary surface and from the head part in the beam exit direction.

4. A dental instrument according to claim 3, wherein the cover plate is fitted in the head part with a seal element so that the gaseous agent can essentially flow off only through the waveguide.

5. A dental instrument according to claim 3, wherein the waveguide is secured in a mount, said mount being held in an easily changeable fashion in the head part.

6. A dental instrument according to claim 3, wherein the gaseous agent first flows into a side of the head part and is then deflected by guide and baffle surfaces transversely relative to the beam exit direction and is finally deflected into the beam exit direction.

7. A dental instrument according to claim 6, wherein the guide and baffle surfaces are arranged to create an asymmetrical flow relative to the boundary surface.

8. A dental instrument for treating teeth with laser beams, said dental instrument comprising a head part; a transmission element being arranged in the head part for outputting the laser beams in a beam exit direction, said transmission element being a lens, which focuses the beams in a free beam onto a focal point situated outside of the head part, said lens having an optical surface forming a boundary surface facing in the beam exit direction; a spacer of material that is non-transmissive for light rays being mounted in the head part following the lens and having an exit aperture, said spacer having a length dimensioned so that the focal point of the lens is located immediately after the exit aperture of the spacer; and means for intruding a flow of a gaseous agent into a side adjacent the lens and then deflecting the flow transversely relative to the beam exit direction across the boundary surface and from the head part in the beam exit direction through the spacer, said means including guide and baffle surfaces.

9. A dental instrument according to claim 8, wherein the spacer is formed of metal.

10. A dental instrument according to claim 8, wherein the spacer has a conical shape tapering to the exit aperture.

11. A dental instrument according to claim 10, wherein the spacer is a metal spacer.

12. A dental instrument according to claim 8, wherein the guide and baffle surfaces are arranged so that the gaseous agent flows asymmetrically across said lens.

* * * * *